United States Patent [19]

Farcasiu et al.

[11] 4,454,364

[45] Jun. 12, 1984

[54] METHODS FOR THE IMPROVEMENT OF TRANSALKYLATION REACTIONS AMONG BENZENOID SPECIES

[75] Inventors: Malvina Farcasiu, Princeton, N.J.; Thomas R. Forbus, Newtown, Pa.

[73] Assignee: Mobil Oil Corporation, New York, N.Y.

[21] Appl. No.: 429,370

[22] Filed: Sep. 30, 1982

[51] Int. Cl.$^3$ ............................................... C07C 5/22
[52] U.S. Cl. .................................... 585/470; 585/472; 585/473; 585/474
[58] Field of Search ............... 585/470, 472, 473, 474; 208/46

[56] References Cited

U.S. PATENT DOCUMENTS 2,739,991 3/1956 Hervert ................................. 585/470
2,834,821 5/1958 Bergsteinsson ...................... 585/470

*Primary Examiner*—Curtis R. Davis
*Attorney, Agent, or Firm*—Alexander J. McKillop; Michael G. Gilman; Charles J. Speciale

[57] ABSTRACT

Methods are provided for effecting the acid catalyzed transfer of alkyl substituents from a first benzenoid specie to a second benzenoid specie at an improved rate. According to a preferred embodiment, the first and second benzenoid species are blended together with an effective amount of acid catalyst. An amount effective to improve the rate of transalkylation of at least one polynuclear aromatic hydrocarbon is then added to the blend which is maintained at a temperature above room temperature for a period of time sufficient to allow a substantial degree of transalkylation to occur.

According to another preferred embodiment, a mixture of benzenoid species such as is found in a fuel or a chemical feedstock is improved through the acid catalyzed transalkylization reaction enhanced by the addition of a polynuclear aromatic hydrocarbon.

12 Claims, 1 Drawing Figure

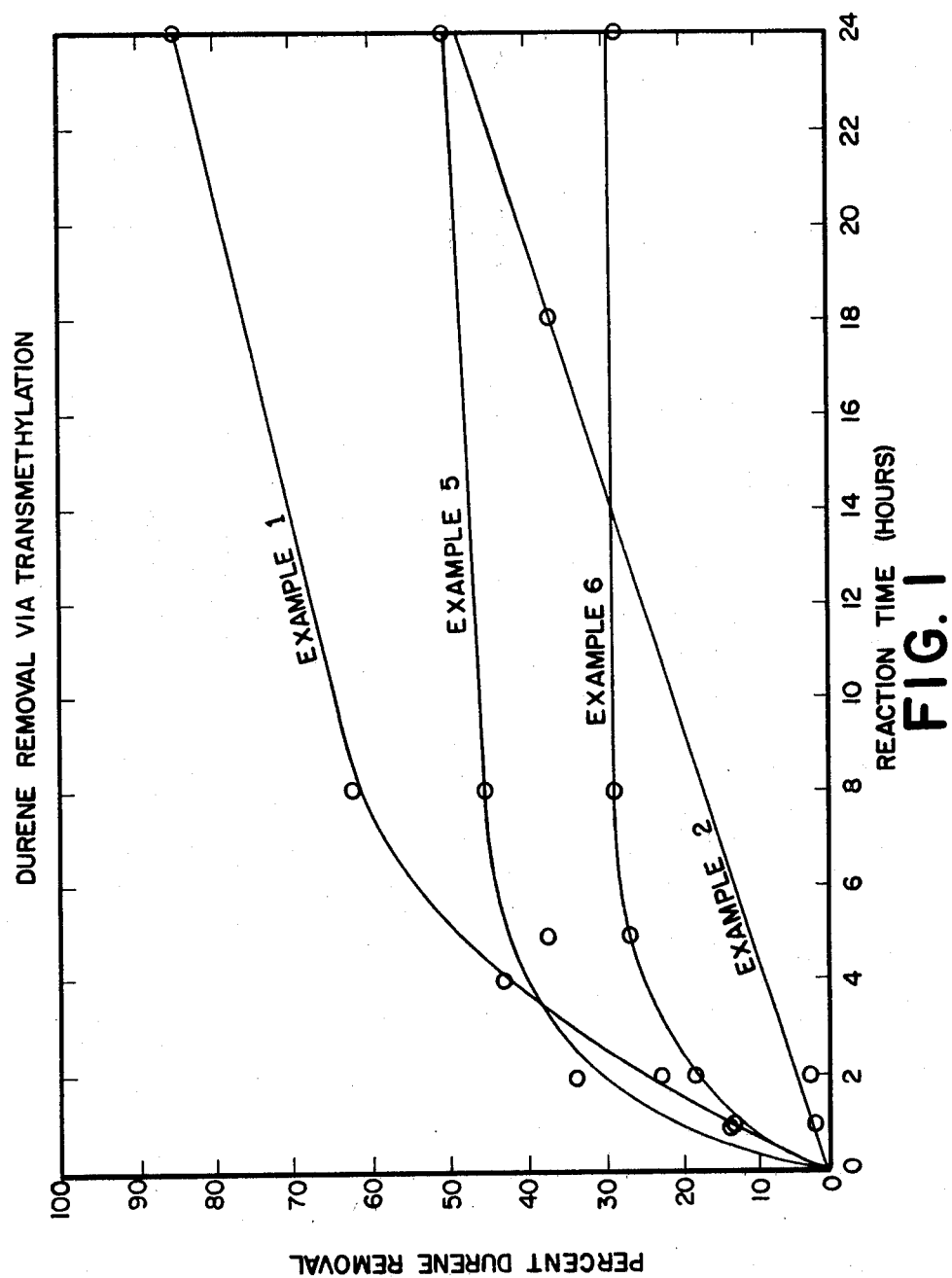

METHODS FOR THE IMPROVEMENT OF TRANSALKYLATION REACTIONS AMONG BENZENOID SPECIES

BACKGROUND OF THE INVENTION

This invention is directed to methods for improving the rates of transalkylation reactions among benzenoid species. This invention is also directed to means for the improvement of mixtures of benzenoid species to improve their utilities for petrochemical and fuel use.

The preparations of alkyl benzenes is known generally to provide products comprising isomeric and stoichiometric mixtures. It is also known to prepare para xylene, 1,4 dimethylbenzene, through a disproportionation reaction of toluene, methylbenzene. This reaction is known to provide a proportion of trimethylbenzene derivatives whose removal is desired from the final product.

Those skilled in the art will appreciate that numerous other examples are known wherein the preparation of certain alkylbenzenes produces a proportion of undesirable polyalkylbenzene byproducts. Such persons will similarly appreciate that the removal of such byproducts from a mixture of benezoid spaces renders the mixture substantially improved from the point of view of efficiency, commercial utility, and product yield. Accordingly, means for such removal are highly desired.

It is known that transalkylation among benzenoid species will take place under acid catalysis at high temperatures. It is also known, however, that acid catalysis will promote intramolecular isomerization of alkyl benzenoids.

The foregoing acid catalyzed transalkylation and isomerization reactions of benzenoids has been used for the removal of undesired polyalkylated benzenes from mixtures of benzenoid species. The rates of the foregoing reactions at low temperature are slow, however; the costs to accomplish such removal of undesired species is concomitantly high.

OBJECTS OF THE INVENTION

It is an object of this invention to provide methods for effecting the transalkylation of alkyl substituents from a first benzenoid species to a second benzenoid species, which reaction proceeds at a relatively high rate.

A further object is to provide means for improvement of petroleum feed stocks and fuels by removing polyalkylated species therefrom.

A further object is to effect the disproportionation of certain alkyl benzenoids into useful products.

A further object is to provide a catalyst for increasing the rate of transalkylation reactions among alkyl benzenoids under acidic conditions.

These and other objects will become apparent from a review of the present specification.

SUMMARY OF THE INVENTION

Methods for improving the transfer of alkyl substituents from a first benzenoid species to a second benzenoid species have been discovered. Accordingly, a first and a second benzenoid species are blended together and acidified with an acid having an acid strength sufficient to promote transalkylation, and being present in such an amount as to provide acid catalysis for the reaction. To the acidified mixture is added an amount effective to improve the rate of the transalkylation reaction of at least one polynuclear aromatic hydrocarbon. The blend is then maintained at a temperature above room temperature for a period of time sufficient to allow a substantial degree of transalkylation to occur.

According to a preferred embodiment, the foregoing method for effecting transalkylation is employed to improve a mixture of benzenoid species such as for use as a fuel substance or for subsequent utility as a petrochemical feedstock.

In general, it has been found that inclusion of a polynuclear aromatic hydrocarbon effects co-catalysis with the acid catalyst; a substantial improvement in reaction rate is realized through such inclusion.

BRIEF DESCRIPTION OF THE DRAWINGS

FIG. 1 is graphical depiction of the rate enhancement experienced through the addition of polynuclear aromatic hydrocarbons in the acid catalyzed transalkylation reaction of benzenoids in accordance with the present invention.

DETAILED DESCRIPTION OF PREFERRED EMBODIMENTS

In accordance with the present invention, it has been found that substantial rate enhancement of the acid catalyzed transalkylation reaction among benzenoid species may be attained through the addition of effective amounts of polynuclear aromatic hydrocarbons to the reaction mixture. Accordingly, it is now possible to remove from complex mixtures of polyalkylbenzenoids certain undesirable species and to do so at more modest costs, at lower temperatures, and in less time. A benzenoid species as contemplated by the present invention is a chemical composition having at least one benzene ring but which is not a polynuclear aromatic hydrocarbon. More particularly, such benzenoid species include the mono-, di-, tri-, tetra-, penta-, and hexamethyl, ethyl, propyl, butyl, and other alkyl benzenes. Also included are benzene species having pluralities of differing alkyl substituents thereupon. In general, such benzenoid species may be represented by the following formula:

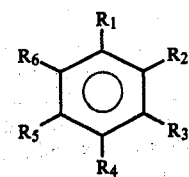

wherein $R_1$–$R_6$ are hydrogen, alkyl, or alkaryl having from one to about 8 carbon atoms and where at least one of $R_1$–$R_6$ is not hydrogen. Also included within the foregoing definition are benzene rings having one or more alkyl substituents attached thereto which are, in turn, substituents of larger systems. Accordingly, biphenyls, triphenyls, and other species may be so included.

It will be appreciated that a transalkylation reaction as contemplated by the present invention transfers an alkyl substituent from one benzenoid species to another benzenoid species. Accordingly, it is preferred that reaction mixtures employed in accordance with the present invention comprise at least two different benzenoid species such as tetramethylbenzene and toluene. Alternatively, a single species may be employed such as toluene to result in a disproportionation reaction, e.g., transmethylation into para xylene and benzene.

While the transalkylation reaction of numerous alkyl substituents on benzenoid species is known, the transmethylation reaction is generally slower than transalkylations involving higher alkyl species, e.g. ethyl, propyl, etc. Accordinly rate enhancement of transmethylation reactions is more economically significant than with the corresponding higher homologs which are, nonetheless, contemplated herein.

Acid catalysis of transalkylation reactions in benzenoid species is well known. Those skilled in the art are familiar with a wide variety of strong acids which are capable of catalyzing such reactions. Such acid catalysis may be either heterogenous or homogeneous; strong acids supported on zeolites or other supports may be employed, however homogenious catalysts are preferred. Convenient acid catalysts include trifluoromethansulfonic acid and other fluorinated homologs thereof. It is preferred that the acid catalyst be a strong acid that has the capability of promoting transalkylation as will be readily apparent to those skilled in the art.

The acid catalyst employed in accordance with the present invention is present in an amount effective to provide acid catalysis for the transalkylation reaction to be accomplished. In general, such acid may be present in an amount from about 2% to about 10% by weight. It is preferred that amounts of about 5% to about 8% be so employed with about 7.5% being most preferred. The actual amount of acid catalyst is not critical to the effectiveness to the present invention save only that an effective amount of catalyst be present.

In accordance with a preferred embodiment of the present invention, at least one of the alkyl substituents on at least one of the benzenoid species is a methyl group. In accordance with another embodiment, one of the benzenoid species is a benzene having at least 3 methyl groups attached thereto. According to yet another embodiment, a first benzenoid species has at least 2 more alkyl substituents thereupon than does a second benzenoid species. Preferably, these alkyl substituents comprise methyl groups.

The rate of acid catalyzed transalkylation among benzenoid species is improved in accordance with the present invention by the addition of an effective amount of a polynuclear aromatic hydrocarbon as co-catalyst. As contemplated herein, a polynuclear aromatic hydrocarbon comprises a chemical species having at least 2 aromatic rings in a fused relationship one to the other. Two aromatic rings are fused one to the other if they share 2 common atoms at adjacent positions on each ring. In general such polynuclear aromatic hydrocarbons will show Huckel aromaticity; they will obey Huckel's rule. See March, *Advanced Organic Chemistry: Reactions, Mechanisms, and Structure* McGraw Hill (1968) pp. 37–54 further to define aromaticity and Huckel's rule. It will be understood that the definition of aromaticity, as explained in the foregoing reference by March, is somewhat ambiguous. Accordingly, it is preferred that a polynuclear aromatic hydrocarbon be defined by what it does rather than by what it is. Such polynuclear aromatic hydrocarbon may be defined as being a chemical species having at least 2 fused rings, which exhibits Huckel aromaticity, and which is capable of enhancing the rate of acid catalyzed transalkylation in benzenoid systems.

Preferred polynuclear aromatic hydrocarbons useful for the practice for one or more embodiments of the present invention comprise 2 or more fused benzene rings. Exemplary members of the foregoing class include naphthalene, anthracene, phenanthrene, chrysene, dibenzenanthracene, benzpyrene, and many others. Additionally, it is likely that heteroatom-containing polynuclear aromatic species may also be employed as long as aromaticity is indicated. Those skilled in the art will appreciate that numerous other polynuclear aromatic hydrocarbons may be employed in the practice of one or more embodiments of the present invention.

An amount of a polynuclear aromatic hydrocarbon which is effective to improve the rate of transalkylation of benzenoid species under acid catalysis will be added to reaction mixture in accordance with the practice of this invention. In general, amounts from about 0.5% to about 5% of such polynuclear aromatic hydrocarbon are preferably employed with from about 1% to about 3% being most preferred.

For the practice of the present invention, it is necessary only to combine in a blend a first benzenoid species and a second benzenoid species, to acidify the blend with an amount effective to provide catalysis for the transalkylation of a strong acid as hereinbefore described, to add to the blend either before or after acidification an effective amount of at least one polynuclear aromatic hydrocarbon and to maintain the blend at a temperature above room temperature until substantial transalkylation occurs. The precise reaction times and temperatures will be dependent upon the particular transalkylation system to be selected. It is preferred that temperatures between about room temperature and 300° C. be employed in the practice of one or more embodiments of the present invention. Substantial improvements in the reaction rates, as evidenced by shortened reaction times for the attainment of particular degrees of transalkylation, will generally be experienced, however.

While the methods of the present invention are suitable to a wide variety of feedstocks, process streams, and product materials, it has been especially effective in reducing the content of durene, 1,2,4,5 tetramethylbenzene, in gasoline or other petroleum distillates.

The foregoing methods are also useful for effecting isomerization of alkyl substituents of benzenoid species and, as such, may facilitate disproportionation reactions such as the aforementioned preparation of para xylene from toluene.

The following examples have been selected to illustrate certain features of the present invention. It is to be understood that such examples are to be considered as illustrative only and not as limiting.

EXAMPLE 1

A molar mixture of one part durene, 5 parts o-xylene, 0.1 parts naphthalene and 0.5 parts trifluoromethanesulfonic acid was refluxed. Aliquots were taken and periodically quenched with base. Analysis of the product mixture by gas chromatography showed a 23% reduction in the concentration of tetramethylbenzene after 2 hours. Durene was specifically reduced by 58% after 2 hours reflux via both transalkylation and isomerization. After 4 hours, the concentration of naphthalene remained essentially unchanged. The data thus collected are displayed in FIG. 1.

EXAMPLE 2

The reaction of Example 1 was duplicated except that the naphthalene was omitted. After 2 hours at reflux, the tetramethylbenzene level was reduced by only 3%.

This data is also displayed in FIG. 1. The durene level was reduced by approximately 35% by isomerization.

EXAMPLE 3

The reaction of Example 1 was duplicated except that 0.1 part pyrene was substituted for the naphthalene. The concentration of tetramethylbenzene was reduced by 29% after 2 hours at reflux via transmethylation.

EXAMPLE 4

The reaction of Example 1 was repeated substituting 0.1 part anthracene for the naphthalene. After 2 hours at reflux, the tetramethylbenzene concentration was reduced by 41%.

EXAMPLE 5

A mixture of 10 parts gasoline having a component of durene therein was combined with one part naphthalene and 1.2 parts trifluoromethanesulfonic acid by weight. The foregoing blend was refluxed and aliquots taken for analysis in accordance with Example 1. After 8 hours of reflux, the durene concentration was reduced by 46% via transalkylation. This data is presented in FIG. 1.

EXAMPLE 6

The procedure of Example 5 was duplicated except that the naphthalene was omitted. After 8 hours of reflux, the durene concentration was reduced by 28% by transalkylation. The data from this example is presented in FIG. 1.

What is claimed is:

1. A method for effecting the transfer of alkyl substituents from a first benzenoid specie to a second benzenoid specie comprising the steps of:
   blending together said first and second benzenoid species;
   acidifying said blend with an amount effective to provide catalysis for said transfer of an acid;
   adding to said blend an amount effective to improve the rate of said transfer of at least one polynuclear aromatic hydrocarbon; and
   maintaining said blend at a temperature above room temperature for a period of time sufficient to allow a substantial degree of said transfer to occur.

2. The method of claim 1 wherein at least one of said alkyl substituents to be transferred is a methyl group.

3. The method of claim 1 wherein said first benzenoid specie is a benzene having at least three methyl groups attached thereto.

4. The method of claim 1 wherein said first benzenoid species has at least two more alkyl substituents thereupon than does said second benzenoid specie.

5. The method of claim 1 wherein said polynuclear aromatic hydrocarbon comprises at least two fused benzene rings.

6. The method of claim 1 wherein said first benzenoid species is a tetramethylbenzene and said blend comprises a petroleum distillate.

7. A method for the improvement of a mixture of benzenoid species, at least one of said species having a plurality of alkyl substituents comprising the steps of:
   acidifying said mixture with an amount of an acid effective to catalyze transalkylation reactions among said species;
   adding to said mixture an amount effective to promote said transalkylation of at least one polynuclear aromatic hydrocarbon; and
   maintaining said mixture at a temperature above room temperature for a period of time sufficient to allow a substantial degree of said transalkylation to occur.

8. The method of claim 7 wherein at least one of said alkyl substituents is a methyl group.

9. The method of claim 7 wherein at least one of said benzenoid species has at least three methyl groups.

10. The method of claim 7 wherein at least a first of said benzenoid species has at least two more alkyl substituents than at least a second of said benzenoid species.

11. The method of claim 7 wherein said polynuclear aromatic hydrocarbon comprises at least two fused benzene rings.

12. The method of claim 7 wherein at least one of said benzenoid species is a tetramethyl benzene and said mixture comprises a petroleum distillate.

* * * * *